United States Patent [19]

Massardo et al.

[11] Patent Number: 4,929,772
[45] Date of Patent: May 29, 1990

[54] PROCESS FOR PREPARING POLYHALOGENATED CARBINOLS

[75] Inventors: Pietro Massardo, Milan; Franco Bettarini, Novara; Paolo Piccardi, Milan; Franco Rama, Varese, all of Italy

[73] Assignee: Istituto Guido Donegani, Milan, Italy

[21] Appl. No.: 321,171

[22] Filed: Mar. 9, 1989

Related U.S. Application Data

[60] Division of Ser. No. 205,506, Jun. 7, 1988, abandoned, which is a continuation of Ser. No. 71,540, Jul. 7, 1987, abandoned, which is a continuation of Ser. No. 817,542, Jan. 10, 1986, abandoned.

[30] Foreign Application Priority Data

Jan. 11, 1985 [IT] Italy ................................ 19080 A/85

[51] Int. Cl.⁵ ............................................ C07C 33/46
[52] U.S. Cl. .................................................... 568/812
[58] Field of Search .......................................... 568/812

[56] References Cited

PUBLICATIONS

Lang, "Chemical Abstract", vol. 106 (1987), 175748J.

*Primary Examiner*—Werren B. Lone
*Attorney, Agent, or Firm*—Stevens, Davis, Miller & Mosher

[57] ABSTRACT

There is disclosed a process for preparing polyhalogenated carbinols having formula:

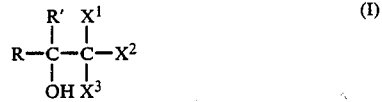

by reacting a compound having formula:

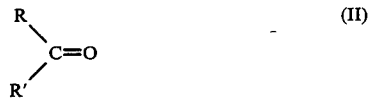

with a system consisting of a compound having formula:

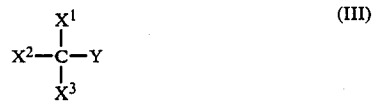

and of a divalent metal or of a metal salt, in protic dipolar solvents, in which formulae R=H, an alkyl, cycloalkyl, alkenyl, cycloalkenyl, alkadienyl, phenyl, naphthyl, anthracyl group, a heterocyclic radical, optionally substituted;

R'=H, a haloalkyl, —CN, —COOR" group with R" equal to H or to an alkyl group;

$X^1$=Cl, Br; =$X_2$=F, Cl, Br;

$X^3$=Cl, Br, $CF_3$, $CCl_3$; Y=Br or Cl when $X^1$, $X^2$ and $X^3$ are different from Br.

1 Claim, No Drawings

PROCESS FOR PREPARING POLYHALOGENATED CARBINOLS

This is a Division of application Ser. No. 205,506 filed June 7, 1988 which in turn is a continuation of application Ser. No. 071,540, filed July 7, 1987, which in turn is a continuation of application Ser. No. 817,542, filed January 10, 1986, all now abandoned.

The present invention relates to a process for preparing polyhalogenated carbinols by reacting a carbonylic compound with a system consisting of a polyhalogenated hydrocarbon and of a divalent metal or of a metal salt in aprotic dipolar solvents.

The polyhalogenated carbinols are important intermediate products in fine chemistry and in particular in the field of pesticides for the preparation, for instance, of benzoylureas and pyrethroides having an insecticidal activity.

BACKGROUND OF THE INVENTION

The literature discloses the preparation of a few polyhalogenated carbinols, in particular the carbinols containing —CCl$_3$ or —CBr$_3$ groups, using synthesis methods different from the present invention, such as, for instance, those described in: Journal of American Chemical Society, 1948, pages 1189 and 1950, pages 5012-14; Bulletin de la Societe Chimie de France, 1967, pages 1520-32; British patent application 2,076,804 and Japanese patent application 77/73.842.

THE PRESENT INVENTION

We have now found a simple and economical method for obtaining polyhalogenated carbinols with good yields. Thus, the object of this invention is a process for preparing polyhalogenated carbinols having general formula:

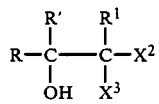

(I)

consisting in reacting a carbonylic compound having formula:

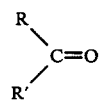

(II)

with a system consisting of a polyhalogenated hydrocarbon having formula:

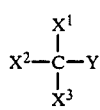

(III)

and of a divalent metal or of a metal salt, in an aprotic dipolar solvent, at temperatures ranging between −20 and the boiling temperature of the solvent, wherein the said formulas
R represents a H atom, an alkyl, cycloalkyl, alkenyl, cycloalkenyl, alkadienyl group, which groups may be substituted, preferably on the first two carbon atoms of the aliphatic chain, by one or more groups selected among a halogen atom, aryl groups, —CN, —NO$_2$, —COOR″ wherein R″ is H or a C$_1$-C$_4$ alkyl group, said R further represents a phenyl, naphthyl, anthracyl group, a heterocyclic radical, optionally substituted by one or more groups selected among halogen atoms, alkyl, alkenyl, alkoxyl, —NO$_2$, —CN, haloalkyl, haloalkenyl, haloalkoxy, thioalkyl, alkylamino, dialkylamino, —COOR″ and —COR″ groups;
R′ represents H, a haloalkyl, —CN, —COOR″ group;
X$^1$ represents Cl, Br;
X$^2$ represents F, Cl, Br;
X$^3$ represents Cl, Br, CF$_3$, CCl$_3$;
Y represents Br or Cl when X$^1$, X$^2$ and X$^3$ are different from Br.

As a metal use may be made, for instance, of: zinc, copper, iron, magnesium, and as metal salt, use may be made, for instance, of stannous chloride.

As solvent there can be used: dimethylformamide, dimethylsulfoxide, hexamethylphosphorotriamide, N-methylpyrrolidone, sulfolane, N,N-dimethylimidazolidinone.

The reactions, which take place successively during the process can be represented schematically according to the following equations:

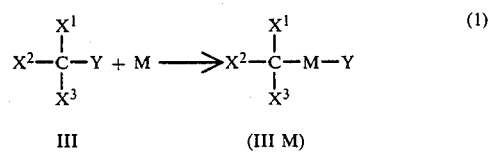

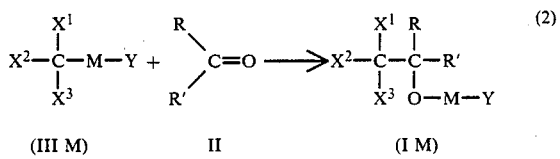

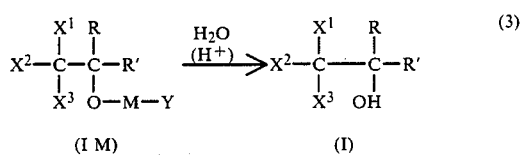

wherein M represents the metal.

The operating conditions for the addition of the reactants in the process, according to the present invention, can vary according to the type of compounds utilized and, in any case, said operating conditions are not a critical factor.

An operating condition concerning the addition consists in adding the metal in only one solution or in subsequent shares to a mixture consisting of hydrocarbon III, of carbonylic compound II and of reaction solvent. Alternatively, hydrocarbon III, optionally dissolved in the reaction solvent, can be added to a suspension of the metal in the reaction solvent, in the presence of carbonylic compound II.

Said operating conditions have to be recommended when the organometallic compound having formula (III M), which forms during the reaction, turns out not to be very stable and therefore tends to give rise to undesirable by-reactions. Should organometallic compound (III M) be sufficiently stable, such as, for instance, 1,1-dichloro-2,2,2-trifluoro-ethyl zinc chloride, it is possible to work according to another operating condition consisting in separately preparing compound (III, M), by heating the metal in a suitable solvent with a slight excess of hydrocarbon III till dissolution and then in mixing said compound with carbonylic compound II dissolved in the reaction solvent.

The process is carried out using the reactants in substantially stoichiometric ratios. However, it would be preferable, according to the characteristics of the concerned reactants, to use an excess with respect to the stoichiometric of both the metal with respect to carbonylic compound II and of hydrocarbon III with respect to the metal.

The compounds of general formula I, wherein $X^3$ represents $CF_3$ and the compounds having general formulas

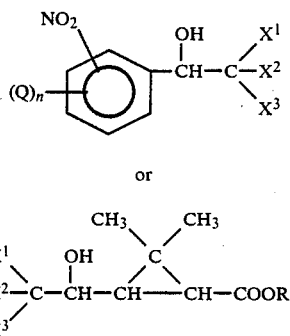

wherein $X^1$, $X^2$, $X^3$ and $R''$ have the meaning as defined in formula (I); Q represents H, a halogen atom, a $C_1$-$C_3$ alkyl group optionally substituted by 1-3 halogen atoms, —$OCH_3$, —$SCH_3$, —$OCF_3$; n is a whole number comprised between 1 and 4, are new compounds and form a further object of the present invention.

Furthermore, we have found that the carbinols having general formula (I) can be reduced to alkenes having general formula:

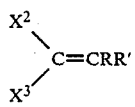

using known methods such as, for instance:
(a) direct treatment of carbinol (I) with zinc in acetic acid;
(b) conversion of carbinol (I) to acetate or to dihalophosphite and subsequent treatment with zinc in dimethylformamide;
(c) substitution of the hydroxyl radical of carbinol (I) with a halogen atom and subsequent dehalogenation by means of zinc.

In the aforesaid conversions, it is generally possible to use carbinol (I) in the same reaction medium in which it has been prepared according to the present invention, namely without isolating it, with considerable economic advantages, as well as with advantages concerning the simplicity of carrying out the process for obtaining the corresponding alkenes.

Alkenes of formula (IV) are, in their turn, important intermediate compounds for the preparation of pesticides. In particular, carbinols of formula (IV) can be reduced, according to the aforesaid methods, to alkenes having formula:

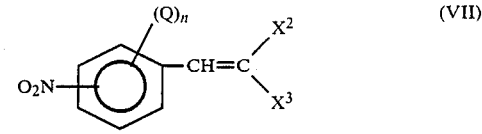

which, after reduction to the corresponding anilines and reaction with suitable isocyanates, provide insecticidal benzoylureas.

The carbinols of formula (V) can be reduced, according to the aforesaid methods, to alkenes of formula:

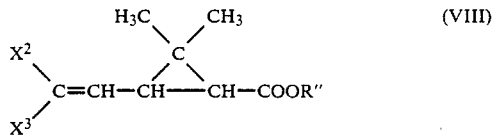

which are successively converted to the respective acid chlorides and then esterified to give rise to pyrethroides, insecticides having a very high activity and a large action spectrum.

The following examples are given to illustrate the invention in more detail but are not intended to be limiting.

EXAMPLE 1

Preparation of 1-phenyl-2,2,2-trichloro-ethanol

A solution containing 3.18 g of benzaldehyde (30 millimoles), 6.16 g of carbon tetrachloride (40 millimoles) in 30 ml of DMF dehydrated on molecular sieves was loaded into a small 3-neck flask having a capacity of 100 ml provided with a reflux cooler, thermometer, magnetic stirrer and kept under a nitrogen atmosphere.

720 mg (30 milligram atoms) of magnesium in the form of shavings were added in doses; in the beginning the mixture was heated to about 40° C., then after the reaction had started, the metal addition and the thermal regulation were checked in order to keep the inner temperature at about 50° C.

When magnesium was almost completely dissolved, the whole was heated at 60° C. for 1 h and then at room temperature overnight.

The mass was then diluted with 250 ml of water, acidified with hydrochloric acid at 10%, extracted with 3 shares of ethyl ether, each of them corresponding to a volume of 80 ml; the organic extract was washed with 50 ml of a saturated solution of sodium chloride, dehydrated with sodium sulphate and concentrated. The residue was analyzed by chromatography on a silica gel column, by eluting with hexane/ethyl acetate in a 95:5 ratio. 3.2 g of the reaction product were obtained.

$^1$H-NMR (CDCl$_3$,TMS), δ (ppm): 3.35 (1H, S); 5.13 (1H, S) 7.1-7.7 (5H, m).

IR (9 cm$^{-1}$): 3440 (—OH).

EXAMPLE 2

Preparation of 1-phenyl-2,2,2-tribromo-ethanol 2.12 g of benzoic aldehyde (20 millimoles), 25 ml of DMF, 6163 g of carbon tetrabromide (20 millimoles) were loaded into a small 3-nect flask having a capacity of 100 ml, provided with a reflux cooler, thermometer, magnetic stirrer, under nitrogen atmosphere.

1.3 g of zinc (20 milligram atoms) were added in small doses in order to keep the temperature at about 45° C., after having finished the addition, the whole was heated at 50° C. for 1 h. The mixture after cooling was poured into 200 ml of water, acidified with HCl at 10%, extracted with 3 portions of ethyl ether each of them corresponding to a volume of 75 ml; the organic extract was washed with a solution of sodium chloride, dehydrated and concentrated.

The product was purified by chromatography on silica gel, by eluting with hexane/ethyl acetate having a 95:5 ratio. 3.3 g of a solid were obtained having a m.p. of 73° C.

$^1$H-NMR (CDCl$_3$, TMS), δ (ppm): 3.80 (1H, S); 5.18 (1H, S) 7.1–7.8 (5H, m).

EXAMPLE 3

Preparation of ethyl 2-hydroxy-2-tribromomethyl-propionate 3.31 g of carbon tetrabromide (10 millimoles), 1.16 g of ethyl piruvate (10 millimoles) and 10 ml of DMF were mixed under nitrogen atmosphere in a small flask having a capacity of 100 ml.

650 mg (10 milligram atoms) of zince in powder were added, in successive portions, under stirring, the temperature of the reaction mixture being kept at about 45° C.

The heating was continued at such temperatures for 2 h, then the mass was diluted with 120 ml of water and 30 ml of a saturated solution of ammonium chloride, extracted with 3 shares of ethyl ether, each of them having a volume of 50 ml, dehydrated with sodium and concentrated in a rotary evaporator. The raw product of reaction was purified by column chromatography by eluting with hexane/ethyl acetate having a 95:5 ratio. 1.6 g of product were obtained.

$^1$H-NMR (CDCl$_3$, TMS), δ (ppm): 1.35 (3H, t); 1.85 (3H, S) 4.35 (2H, q); 4.45 (1H, S).

IR (cm$^{-1}$): 3460 (—OH); 1740 (—COOEt).

EXAMPLE 4

Preparation of ethyl 2-(2,2-dichloro-1-hydroxy-3,3,3-trifluoropropyl)-3,3-dimethyl-cyclopropane-carboxylate 9.8 g of Zn in powder (0.15 gram atoms) and 37.5 g of 1,1,1-trichloro-2,2,2-trifluoro-ethane (0.2 moles) in 125 ml of anhydrous THF were reflux heated under nitrogen atmosphere until the metal was dissolved, after which solvent and freon in excess were removed by distillation at reduced pressure.

The residue was dissolved in 50 ml of DMF and 17 g (0.1 moles) of ethyl 3,3-dimethyl-2-formyl-cyclopropanecarboxylate (cis-trans mixture) dissolved in 50 ml of DMF were added to said solution.

Always under nitrogen atmosphere and under stirring, the mass was heated at 45° C. for 5 hours. After cooling it was diluted with 500 ml of acidulated water and extracted with 3 shares of ethyl ether, each of them having a volume of 150 ml. The extract was washed with a solution of sodium chloride (100 ml), then dehydrated and concentrated.

After separation by column chromatography (eluent hexane/ethyl acetate 95:5) 19,5 g of carbinol (cis-trans mixture 45:55) were obtained.

$^1$H-NMR (CDCl$_3$, TMS), δ (ppm): 1.1–1.4 (9H, m); 1.55–2.1 (2H, m); 2.7 (1H, S); 3.75 (1H, d); 4.08 (2H, q).

EXAMPLE 5

Preparation of 2,2-dibromo-3,3,3-trifluoro-1-(2-chlorophenyl) propanol

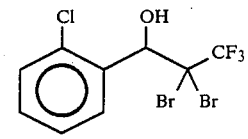

83.5 g of CF$_3$CBr$_3$ in anhydrous DMF and 28 g of 2-chlorobenzaldehyde were reacted under a nitrogen atmosphere. The mixture was brought to 5° C. and zinc in powder (g. 16.0) was added to it slowly. Then the mixture was let reach the room temperature and kept under stirring for 6 hours. The mixture was poured into water and extracted three times with ethyl ether.

The ethereal extract was shaken with an aqueous solution of sodium bisulfite in order to eliminate the non-reacted aldehyde, and then was dehydrated with anhydrous sodium sulphate. After filtration, the residue was concentrated under vacuum and purified by chromatography on silica gel, by eluting with hexane/ether 95:5. 30 g of product were thus obtained.

$^1$H-NMR (δ, THS=0); 8.0–7.4 (m, 4H, Arom.); 6.9 (d, 1H, CH); 3.3 (s broad, 1H, OH).

EXAMPLE 6

Preparation of 2,2-dichloro-3,3,3-trifluoo-1-phenyl propanol

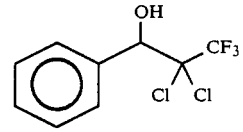

3 g of benzaldehyde and 5.3 g of CF$_3$-CCL$_3$ were reacted in 30 ml of anhydrous DMSO, under nitrogen atmosphere. 5.3 g of anhydrous SnCl$_2$ were added at room temperature and the mixture was kept at room temperature under stirring for 10 hours. Then the whole was poured into water and extracted with ether.

The ethereal solution was shaken with a solution of sodium bisulfite in order to eliminate the non-reacted benzaldehyde and then dehydrated on anhydrous sodium sulphate. The ether was removed under vacuum and 4.4 g of product were obtained.

$^1$HMNR (CDCl$_3$, TMS) δ (ppm); 2.9 (1H, S) OH; 5 (1H, S) CH; 7.2 (5H, m) aromatic.

EXAMPLE 7

Preparation of 2,2-dichloro-3,3,3-trifluoro-1-(3-pyridyl-1-propanol)

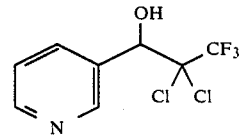

5 g of 3-pyridine-carboxy-aldehyde in 100 ml of anhydrous DMF and 34 g of CF$_3$CCl$_2$. ZnCl prepared previously were reacted under a nitrogen atmosphere. The mixture was heated at 40° C. for 4 h, then poured into water and extracted with ether several times. The collected organic extract was dehydrated on anhydrous sodium sulphate and then concentrated under vacuum. 9 g of a white solid were obtained having a melting point of 141°-143° C.

EXAMPLE 8

Preparation of 2,2-dichloro-3,3,3-trifluoro-1-(4-nitrophenyl)-propanol

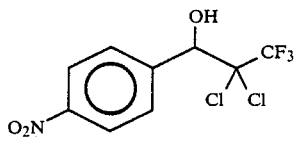

0.066 moles of p-nitrobenzaldehyde and 0.080 moles of the complex Zn-CF$_3$CCl$_3$ prepared previously were reacted in 100 ml of anhydrous DMF under a nitrogen atmosphere. The whole was heated at 35°-40° C. for 3 h, then poured into water, acidified with dilute HCl and extracted 3 times with ethyl ether. The collected organic extract was brought to a neutral pH by washings with water and, after dehydration on anhydrous sodium sulphate was concentrated under vacuum.

18 g of a clear solid were thus obtained, having a melting point of 102° C.

EXAMPLE 9

Preparation of 2,2-dichloro-3,3,3-trifluoro-1-(2,6-dichloro-4-nitrophenyl)-1-propanol

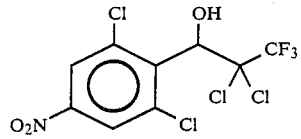

3 g of 2,6-dichloro-4-nitro benzaldehyde were reacted, in 20 ml of anhydrous DMF under a nitrogen atmosphere, with CF$_3$CCl$_2$ZnCl prepared from 5 g of CF$_3$CCl$_3$ and 2.2 g of Zn in 10 ml of THF at 60° C. for 1 hour. The mixture was heated at 50° C. for 2 hours and at the end of the reaction it was poured into acidulated water and extracted repeatedly with ethyl ether.

After having removed the ethyl ether under vacuum, 3.5 g of product were obtained.

$^1$H-NMR (CDCl$_3$, TMS) δ (ppm): 4.3 (1H, d); 6.35 (1Hd); 8.15 (2H, s).

EXAMPLES 10-24

By working under the operating conditions of the preceding examples, 15 carbinols were prepared, the characteristics of which are reported in the Table.

TABLE

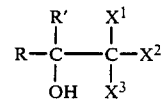

| Ex. No. | R | R' | X$^1$ | X$^2$ | X$^3$ | $^1$H-NMR (δ, TMS = O) | Mass spectrum m.p. |
|---|---|---|---|---|---|---|---|
| 10 | ∧∧∧ | H | Cl | Cl | CF$_3$ | — | m/e 223; 181; 156; 151; 101; 55 (base peak) |
| 11 | ∧∧ | H | Br | Br | Br | — | m/e 279; 243; 73; 55 (base peak) m.p. 54-55° |
| 12 | —CCl$_3$ | H | Cl | Cl | CF$_3$ | — | m/e 263; 181 (base peak) 151; 147; 111 |
| 13 | (thiophene) | H | Cl | Cl | CF$_3$ | 7.6-6.8 (m, 3H); 5.4 (s broad, 1H); 3.9 (s broad, 1H | m/e 264 (H$^f$); 247; 212; 113(base peak) |
| 14 | 3,4-(H$_3$C—O)$_2$C$_6$H$_3$— | H | Cl | Cl | CF$_3$ | 7.1-6.7 (m, 3H, Arom) 5.2 (d, 1H, CH); 3.9 (s, 6H, CH$_3$); 3.2 (d, 1H, OH) | m.p. 118-120° C. |
| 15 | 4-Br, 2-OH-C$_6$H$_3$— | H | Cl | Cl | CF$_3$ | 10.9 (s, 1H, phenolic OH); 7.5-6.7 (m, 3H Arom); 5.5 (s, 1H, CH 4.5 (broad, OH, OH) | — |
| 16 | (naphthyl) | H | Cl | Cl | CF$_3$ | 7.9-7.4 (m, 7H, Arom) 5.3 (s broad, 1H, CH); 3.7 (s broad, 1H, OH) | m.p. 56-58° C. |
| 17 | OHCCH$_2$— | H | Cl | Cl | CF$_3$ | — | m/e 206; 178; 171; |

TABLE-continued $$R-\underset{\underset{OH}{|}}{\overset{\overset{R'}{|}}{C}}-\underset{\underset{X^3}{|}}{\overset{\overset{X^1}{|}}{C}}-X^2$$

| Ex. No. | R | R' | X¹ | X² | X³ | ¹H-NMR (δ, TMS = 0) | Mass spectrum m.p. |
|---|---|---|---|---|---|---|---|
| | | | | | | | 151; 109; 45 (base peak) |
| 18 | $CH_3-CH_2-CH_2-CH=CH-$ (CH₃-CH(CH₂)-CH₂-CH=CH-) | H | Cl | Cl | CF₃ | — | m/e 221; 156; 151; 99; 57 (base peak) |
| 19 | H₃C, CH₃ cyclopropyl-COOC₂H₅ | H | Br | Br | CF₃ | 4.1 (q, 2H, CH₂); 3.7 (d, 1H, CHOH); 2.8 (s broad, 1H, OH); 2.1–1.6 (m, 2H); 1.4–1.2 (m, 9H, CH₃) | — |
| 20 | H₃C, CH₃ cyclopropyl-COOC₂H₅ | H | Br | F | CF₃ | — | m/e 335; 305; 225; 179; 141 |
| 21 | H₃C, CH₃ cyclopropyl-COOC₂H₅ | H | Br | Br | Br | 4.1 (q, 2H, CH₂); 3.7 (d, 1H, CH—OH); 3.0 (s, broad, 1H, OH; 1.8–1.6 (m, 2H, CH—CH; 1.4–1.2 (m, 9H, CH₃) | — |
| 22 | 2-CHO-phenyl | H | Cl | Cl | Cl | 10.6 (s, 1H, CHO); 8.1–7.4 (m, 4H, Arom); 5.3 (s, 1H, CH); 4.7 (broad 1H, OH) | — |
| 23 | 4-CHO-phenyl | H | Cl | Cl | CF₃ | 9.9 (s, 1H, CHO); 8.1–7.8 (q, 4H, Arom); 5.5 (s, 1H, CH); 3.8 (broad, 1H, OH) | — |
| 24 | 2-furyl | H | Cl | Cl | CF₃ | 7.4 (t, 1H) + 6.4 (dd, 2H, Arom); 5.2 (d broad, 1H, CH); 3.8 (d, broad, 1H, OH) | — |

EXAMPLE 25

Preparation of ethyl 2-(2-chloro-3,3,3-trifluoro-2-propenyl)-3,3-dimethyl-cyclopropanecarboxylate 1.6 g (5 millimoles) of ethyl 2-(2,2-dichloro-1-hydroxy-3,3,3-trifluoro-propyl)-3,3-dimethyl-cyclopropanecarboxylate, prepared as described in Example 4, were dissolved in 10 ml of DMF and 5 ml of pyridine; 1 ml of acetic anhydride was added to the mixture, that was kept at room temperature for 2 h under stirring.

When all the carbinol was converted into acetate (gaschromatographic control), 520 mg (8 milligram atoms) of zinc in powder were added and the mixture was heated at 60° C. for 2 h. The mixture was then treated under the usual conditions and the residue was purified chromatography on silica gel. 1.2 g of the desired product were obtained.

¹H-NMR (CDCl₃, TMS, (ppm): 1.1–1.4 (9H, m); 1.65–2.55 (2H, m); 4.1 (2H, q); 5.7–6.2 (1H, m).

EXAMPLE 26

Preparation of 3,5-dichloro-4-(2-chloro-3,3,3-trifluoro-1-propenyl)-aniline (intermediate for insecticides)

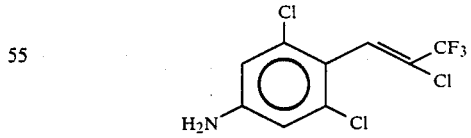

3.5 g of 2,2-dichloro-3,3,3-trifluoro-1-(2,6dichloro-4-nitrophenyl-1-propanol, prepared as described in Example 9, were dissolved in pyridine (15 ml) and treated with 1.5 g of acetic anhydride.

After 3 h the whole was poured into water and ice and then extracted 3 times with ether using 70 ml at a time. The ethereal phase was washed with N/10 HCl in order to eliminate the excess pyridine, and neutralized with sodium bicarbonate in a saturate solution. The ether was then removed thereby obtaining 3.4 g of acetate. 0.6 g of acetate were treated with 0.95 g of iron in powder in 6 ml of ethanol and 1.5 ml of $H_2O$ acidified with 0.05 ml of concentrated HCl. The mixture was heated at 80° C. for 4 h, then poured into water, brought to pH 9 and extracted 3 times with 50 ml of ethyl ether at a time.

After drying on sodium sulphate, 0.33 g of aniline were obtained.

$^1$H-NMR (CDCl$_3$, TMS), δ (ppm); 3.9 (2H, broad); 6.6 (2H, s); 7.2 (1H, s).

EXAMPLE 27

Preparation of 2-chloro-3,3,3-trifluoro-1-phenyl-propene

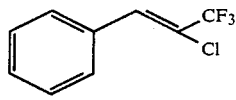

20 ml of DMF, 3500 g of benzaldehyde and 3,160 g of CF$_3$CCl$_3$ were loaded into a 50 l flask under a nitrogen atmosphere. The temperature was brought to −5° C., 2 g of bisublimed I$_2$ were added and then, in small shares, over about 2 h, Zn (3,313 g) in powder previously activated in order to restrain the reaction exothermicity. The temperature was let reach 15° C. and after 15 minutes 5 l of acetic anhydride were added to the mixture. The temperature was brought to 55° C. and after 1 h a further amount of Zn in powder (2,800 g) was added. The whole was heated at 80° C. for 1½ h, then cooled, and poured into H$_2$O. The mass was acidified with HCl and extracted at room temperature with 30 l of CH$_2$Cl$_2$ (twice).

The organic extract was washed till neutral pH and concentrated. The residue (6,920 g) was distilled at reduced pressure thereby obtaining 5,185 g of prodcut (m.p. 61° C. at 4 mm Hg).

We claim:

1. A polyhalogenated carbinol of the formula:

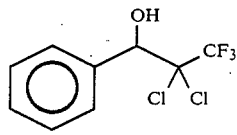

* * * * *